United States Patent [19]

Cuberes-Altisent et al.

[11] Patent Number: 5,214,040
[45] Date of Patent: May 25, 1993

[54] NONSADITIVE ANTIHISTAMINICS DERIVED FROM BENZIMIDAZOLES

[75] Inventors: Maria R. Cuberes-Altisent; Jordi Frigola-Constansa; Juan Pares-Corominas, all of Barcelona, Spain

[73] Assignee: Laboratorios del Dr. Esteve, S.A., Barcelona, Spain

[21] Appl. No.: 863,208

[22] Filed: Apr. 3, 1992

[30] Foreign Application Priority Data

Apr. 5, 1991 [FR] France ............... 91 04171

[51] Int. Cl.$^5$ .................. A61K 31/55; C07D 403/14
[52] U.S. Cl. .................................. 514/218; 540/575
[58] Field of Search ................. 540/575; 514/218

[56] References Cited

U.S. PATENT DOCUMENTS 4,200,641 4/1980 Vandenberk et al. ............... 424/267
5,010,075 4/1991 Pascal et al. ....................... 540/575

Primary Examiner—Patricia L. Morris
Attorney, Agent, or Firm—Dressler, Goldsmith, Shore, Sutker & Milnamow

[57] ABSTRACT

The present invention relates to novel benzimidazole derivatives characterized in that they are of the general formula I, and their therapeutically acceptable salts,

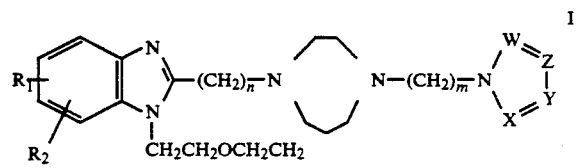

in which:

$R_1$ and $R_2$, which are identical or different, represent a hydrogen or a halogen atom, a lower alkyl radical, a hydroxyl radical, an alkoxy radical, an alkyl carboxylate radical, or an aryl or substituted aryl radical, n may take the values 0 or 1, m may take the values 2 to 4, X, Y, Z and W, which are identical or different, and which may even form part of another aromatic or nonaromatic ring, represent a nitrogen atom or a carbon atom linked to a hydrogen or to a halogen atom, or to another alkyl, aryl, carboxyalkyl, carboxylic, hydroxyl, alkyl hydroxyl, sulphonic or alkylsulphonic radical.

3 Claims, No Drawings

NONSADITIVE ANTIHISTAMINICS DERIVED FROM BENZIMIDAZOLES

The present invention relates to novel benzimidazole derivatives, to their method of preparation and to their use as medicinal products.

The compounds which are the subject of the present invention are of the general formula I

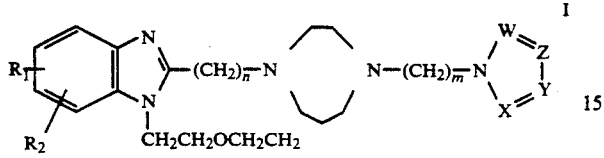

in which:

R$_1$ and R$_2$, which are identical or different, represent a hydrogen or a halogen atom, a lower alkyl radical, a hydroxyl radical, an alkoxy radical, an alkyl carboxylate radical, or an aryl or substituted aryl radical, n may take the values 0 or 1, m may take the values 2 to 4, X, Y, Z and W, which are identical or different, and which may even form part of another aromatic or nonaromatic ring, represent a nitrogen atom or a carbon atom linked to a hydrogen or to a halogen atom, or to another alkyl, aryl, carboxyalkyl, carboxylic, hydroxyl, alkylhydroxyl, sulphonic and alkylsulphonic radical.

Benzimidazole derivatives are already known in the scientific literature which possess various biological activities such as for example analgesic and anti-inflammatory activities (*Japan Kokai* 75, 126, 682), anti-gastric secretion activity (EP 246,126 and EP 5129); antihistaminic activity (J. Jilek et al., *Collect. Czech. Chem. Commun.* 1988, 53, 870-83; U.S. Pat. No. 4,200,641; *Drugs of the Future*, VII; 10-1, 1982; R. Iemura et al., *J. Med. Chem.*, 1986, 29, 1178-1183; R. Iemura et al., *J. Heteroxycyclic. Chem.*, 1987, 24, 31-37; French Patent Application FR 90/09563). The compounds which are the subject of the present invention are novel benzimidazole derivatives, namely 1-(2-ethoxyethyl)-2-{ω[ω(azol-1-yl)alkyl]exahydro-1,4-diazepin-1-ylalkyl}benzimidazole, which will be named in this invention as 1-(2-ethoxyethyl)-2-{ω[ω(azol-1-yl)alkyl]homopiperazin-1-ylalkyl}benzimidazole. We have discovered that these novel derivatives possess a very good antihistaminic activity and have no side effects on the central nervous system.

The novel derivatives of general formula I may be prepared, in accordance with the invention, using any one of the following methods:

Method A

By reacting a compound of general formula IIa

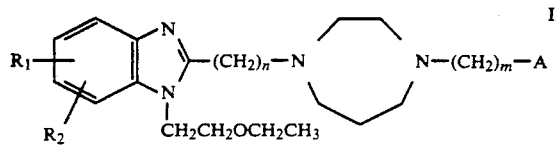

or alternatively IIb

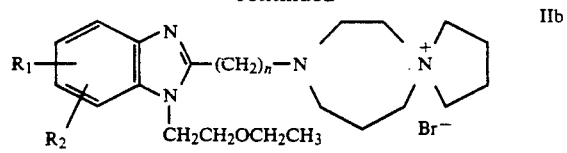

in which R$_1$, R$_2$, n and m have the meanings given above, and A represents a halogen atom or a good "departing group" chosen from tosyloxy or mesyloxy, with a compound of general formula III

in which X, Y, Z and W have the meanings given above.

The reaction is carried out in the presence of a suitable solvent, for example dimethyl sulphoxide, dimethylformamide, alcohols, aromatic or nonaromatic hydrocarbons, ethers such as dioxane or diphenyl ether, or of mixtures of these solvents. This reaction is advantageously carried out in the presence of a base such as alkali metal hydroxides, carbonates, or bicarbonates, or alternatively of a mixture of these bases. Alkali metal hydrides may also be used. The most suitable temperatures vary between room temperature and the reflux temperature of the solvent, and the reaction time is between 1 hour and 24 hours.

Method B

By reacting a compound of general formula IIa, in which A represents a radical —NH$_2$, with 2,5-dimethoxytetrahydrofuran.

The reaction is carried out in the presence of a suitable solvent, for example acetic acid, water, alcohols, ketones or of mixtures of these solvents. The most suitable temperatures vary between room temperature and the reflux temperature of the solvent, and the reaction time is between a few minutes and 24 hours.

Method C

By reacting a compound of general formula IV

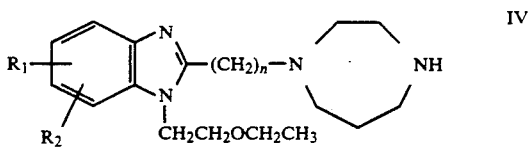

in which R$_1$, R$_2$ and n have the meanings given above, with a compound of general formula V

where X, Y, Z, W and m have the meanings given above, and B represents a halogen atom or a good "departing group" chosen from tosyloxy or mesyloxy.

The reaction is carried out in the presence of a suitable solvent, for example, dimethyl sulphoxide, dimethylformamide, alcohols, aromatic or nonaromatic hydrocarbons, ethers such as dioxane or diphenyl ether, or of mixtures of these solvents. This reaction is advantageously carried out in the presence of a base such as alkali metal hydroxides, carbonates or bicarbonates, or alternatively of a mixture of these bases. The most suitable temperatures vary between room temperature and the reflux temperature of the solvent, and the reaction time is between 1 hour and 24 hours.

The preparation of the novel derivatives according to the invention is given in the, following examples. The examples below, given simply by way of illustration, should not, however, limit in any manner the scope of the invention.

Method A

Example 1

Preparation of
1-(2-ethoxyethyl)-2-{4-[4-(pyrazol-1-yl)butyl]homopiperazin-1-ylmethyl}benzimidazole a) 1-(2-ethoxyethyl)-2-(4-benzyl-1H-homopiperazin-1-ylmethyl)benzimidazole.

A solution of 13.6 g (42.5 mmol) of 1H-2-((4-benzyl-1H-homopiperazin-1-yl-methyl)benzimidazole in 20 ml of dimethylformamide (DMF) is slowly added to a suspension of 2.04 g (46.7 mmol) of NaH (55% in mineral oil). The mixture is heated to 60°–70° C. for 1 hour, and a solution of 5.1 g (46.7 mmol) of 1-chloro-2-ethoxyethane in 5 ml of DMF is then added.

The mixture is maintained stirring, under the same conditions for 5 hours. It is poured into water and extracted with ethyl acetate, washed with water, the organic phase dried using $Na_2SO_4$, filtered and evaporated. The resulting oil is purified on a silica chromatography column. Elution with chloroform-methanol 99:1 gives 5.65 g (50%) of 1-(2-ethoxyethyl-2-(4-benzyl-1H-homopiperazin-1-yl-methyl)benzimidazole, and elution with chloroform-methanol 97:3 gives 4.3 g (32%) of unreacted starting product.

$^1$H-NMR ($CDCl_3$): δ1.12 (t,3 H); 1.79 (m,2 H); 2.69 (m,8 H); 3.41 (q,2 H); 3.63 (s,2 H); 3.76 (t,2 H); 3.98 (s,2 H); 4.55 (t,2 H); 7.25 (m,8 H); 7.7 (m,1H).

b) 1-(2-ethoxyethyl)-2-(homopiperazin-1-yl-methyl)-benzimidazole.

A solution of 5.94 g (15.15 mmol) of 1-(2-ethoxyethyl)-2-(4-benzyl-1H-homopiperazin-1-yl-methyl)benzimidazole in 80 ml of 80% acetic acid is heated at 60° C. with 4.02 g of 5% Pd/C (water content: 50%) under a 5 atm. hydrogen atmosphere, for 16 hours. The mixture is filtered and evaporated to dryness. The residue is taken up in chloroform and washed with 20% NaOH, with water, and dried using $Na_2SO_4$, filtered and evaporated. 3.65 g (80%) of 1-(2-ethoxyethyl)-2-(homopiperazin-1-yl-methyl)benzimidazole are obtained.

$^1$H-NMR ($CDCl_3$): δ1.12 (t,3 H); 1.78 (m,2 H); 2.28 (broad s, 1H); 2.74–3.05 (m,8 H); 3.41 (q,2 H); 3.76 (t,2 H); 4.02 (s,2 H); 4.56 (t,2 H); 7.25 (m,3 H); 7.7 (m,1H).
IR(film): 3312, 1463, 1119, 744 cm$^{-1}$ c) 1-(2-ethoxyethyl)-2-(8-methylaza-5-azoniaspiro[4.6]undecane)benzimidazole.

A mixture of 4 g (13.24 mmol) of 1-(2-ethoxyethyl)-2-(homopiperazin-1-yl-methyl)benzimidazole, 3.29 g (15.23 mmol) of 1,4-dibromobutane and 2.5 g (18.1 mmol) of potassium carbonate in 40 ml of chloroform, is refluxed for 16 hours. The mixture is cooled, filtered and evaporated. The residue is triturated in ethyl ether and 5.6 g (97%) of a hygroscopic solid are obtained, which solid is used as it is without further purification.

$^1$H-NMR($CDCl_3$): δ1.06 (t,3 H); 2.24 (m,6 H); 2.96–3.51 (m,8 H); 3.72–3.90 (m,8 H); 4.15 (s,2 H); 4.53 (t,2 H); 7.30 (m,3 H); 7.74 (m,1H).

d) 1-(2-ethoxyethyl)-2-{4-[4-(pyrazol-1-yl)butyl]-homopiperazin-1-yl-methyl}benzimidazole.

A mixture of 3 g (6.86 mmol) of 1-(2-ethoxyethyl)-2-(8-methylaza-5-azoniaspiro[4.6]undecane)benzimidazole bromide, 0.56 g (8.24 mmol) of pyrazole, 1.8 g (13 mmol) of potassium carbonate and 30 ml of dimethylformamide is refluxed for 16 hours. The mixture is cooled, filtered and the filtrate is evaporated to dryness. The residue is taken up in chloroform and washed with water. The organic phase is dried using $Na_2SO_4$, filtered and evaporated. The resulting oil is purified on a silica chromatography column (eluent: chloroform-methanol 9:1). 1.40 g (48%) of 1-(2-ethoxyethyl)-2-{4-[4-(pyrazol-1-yl)butyl]homopiperazin-1-yl-methyl}benzimidazole are thus obtained in oil form.

The spectroscopic data for its identification are presented in Tables 1 and 2.

Example 3

Preparation of
1-(2-ethoxyethyl)-2-{4-[4-(4,5-dichloro-2-methylimidazol-1-yl)butyl]homopiperazin-1-yl-methyl} benzimidazole The preparation is carried out in a manner quite similar to that presented in Example 1, with a yield of 36%.

The spectroscopic data for its identification are presented in Tables 1 and 2.

Example 5

Preparation of
1-(2-ethoxyethyl)-2-{4-[4-(4-carboxypyrazol-1-yl)butyl]homopiperazin-1-yl}benzimidazole a) 1-(2-ethoxyethyl)-2-(8-aza-5-azoniaspiro[4.6]-undecane)benzimidazole.

The preparation is carried out using the same procedure as that presented in Example 1c, with a yield of 97%.

$^1$H-NMR ($CDCl_3$): δ1.09 (t,3 H); 1.9–2.4 (m,6 H); 3.42 (q,2 H); 3.82 (t,2 H); 3.9–4.1 (m,12 H); 4.26 (t,2 H); 7.20 (m,3 H); 7.50 (m,1H).

b) 1-(2-ethoxyethyl)-2-{4-[4-(4-ethyloxycarbonylpyrazol-1-yl)butyl]homopiperazin-1-yl}benzimidazole.

The preparation is carried out using the same procedure as that presented in Example 1d, and the crude product is obtained, which is purified on a silica chromatographic column (eluent:chloroform-methanol95:5). Yield 35%.

$^1$H-NM2 ($CDCl_3$): δ1.13 (t,3 H); 1.33 (t,3 H); 1.93 (m,6 H); 2.6 (t,2 H); 2.8 (m,4 H); 3.35–3.82 (m,8 H); 4.07–4.4 (m,6 H); 7.1–7.25 (m,3 H); 7.5 (m,1H); 7.85 (s,2 H).

The ester prepared above is hydrolysed by treating a solution in ethanol with 10% sodium hydroxide for 15 hours at room temperature. The alcohol is evaporated and the aqueous solution is neutralised with hydrochloric acid. It is evaporated to dryness and the acid is extracted from the residue by digestion with isopropanol. Yield 87%. Melting point >300° C.

The spectroscopic data for its identification are presented in Tables 1 and 2.

Method B

Example 2

Preparation of
1-(2-ethoxyethyl)-2-{4-[4-(pyrrol-1-yl)butyl]homopiperazin-1-yl-methyl}benzimidazole A solution of 2.98 g (8 mmol) of 1-(2-ethoxyethyl)-2-{4-(4-aminobutyl)homopiperazin-1-yl-methyl}benzimidazole and 1.06 g (8 mmol) of 2,5-dimethoxytetrahydrofuran in 30 ml of acetic acid is refluxed for 25 minutes. The mixture is cooled, poured into ice cold water, neutralised with NaHCO$_3$ and extracted with chloroform. It is dried using Na$_2$SO$_4$ and evaporated to dryness under vacuum. 3.2 g of the crude compound are thus obtained which are purified on a silica chromatography column (eluent: chloroform-methanol 92:8). Yield 51%.

The spectroscopic data for the compound are the same as those presented in Example 2 of method C.

Method C

Example 2

Preparation of 1-(2-ethoxyethyl)-2 {4-[4-(pyrrol-1-yl)butyl]homopiperazin-1-yl-methyl} benzimidazole A mixture of 2.42 g (8 mmol) of 1-(2-ethoxyethyl)-2-(homopiperazin-1-yl-methyl)benzimidazole, 1.39 g (8.8 mmol) of 1-(4-chlorobutyl)pyrrole, 1.65 g (12 mmol) of potassium carbonate and 1.65 g (11 mmol) of sodium iodide in 40 ml of methyl ethyl ketone is refluxed for 16 hours. The mixture is cooled, filtered and the filtrate evaporated to dryness. The residue is taken up in chloroform and washed with water, dried, filtered and evaporated under vacuum. The resulting product is purified on a silica chromatographic column (eluent: chloroform-methanol 92:8) and 1.9 g (56%) of 1-(2-ethoxyethyl)-2-{4-[4-(pyrrol-1-yl)butyl]homopiperazin-1-yl-methyl}benzimidazole are obtained.

The spectroscopic data for its identification are presented in Tables 1 and 2.

Example 4

Preparation of
1-(2-ethoxyethyl)-2-{4-[4-(pyrazol-1-yl)butyl]homopiperazin-1-yl}benzimidazole The preparation is carried out in a manner quite similar to the procedure in the example above, and the compound, whose salt with maleic acid has a melting point of 102°-105° C., is obtained with a yield of 49%.

TABLE I

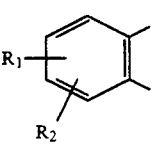

| Example no. | R$_1$ | R$_2$ | n | m | R | Method | IR (cm$^{-1}$) (film) |
|---|---|---|---|---|---|---|---|
| 1 | H | H | 1 | 4 | 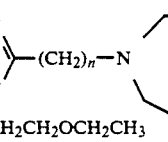 | A C | 2938, 2869, 1464, 1119, 748, 619 |
| 2 | H | H | 1 | 4 | 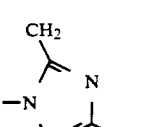 | B C | 2936, 2870, 1463, 1120, 745, 725 |
| 3 | H | H | 1 | 4 | 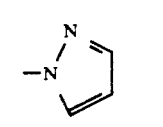 | A | 2937, 1464, 1408, 1246 1120, 746 |
| 4 | H | H | 0 | 4 | 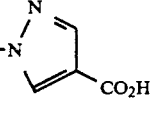 | C | maleate (KBr): 3000, 2890, 1619, 1579, 1470, 1358 |
| 5 | H | H | 0 | 4 | 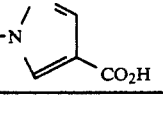 | A | 3600–3150, 1571, 1432, 670 |
| 6 | H | H | 0 | 4 | 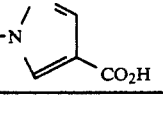 | A | 1715, 1565, 1465, 1120, 1040, 750 |

TABLE 2

| Example no. | ¹H-NMR (CDCl₃) δ |
|---|---|
| 1 | 1.11(t, 3H); 1.41(m, 2H); 1.79(m, 4H); 2.37-2.74 (m, 10H); 3.39(q, 2H); 3.75(t, 2H); 3.96(s, 2H); 4, 12(t, 2H); 4.55(t, 2H); 6.22(broad s, 1H); 7.2-7.47(m, 5H); 7.68(m, 1H) |
| 2 | 1.11(t, 3H); 1.47(m, 2H); 1.82(m, 4H); 2.48 (t, 2H); 2.73(m, 8H); 3.39(q, 2H); 3.75(t, 2H); 3.87(t, 2H); 3.97(s, 2H); 4.53(t, 2H); 6.11(m, 2H); 6.63(m, 2H); 7.25(m, 3H); 7.67(m, 1H) |
| 3 | 1.11(t, 3H); 1.5-1.9(m, 6H); 2.36(s, 3H); 2.5-2.9(m, 10H); 3.39(q, 2H); 3.7-3.9(dt, 4H); 3.99(s, 2H); 4.54(t, 2H); 7.26(m, 3H)7.68 (m, 1H) |
| 4 | 1.13(t, 3H); 1.46(m, 2H); 1.95(m, 4H); 2.52 (t, 2H); 2.79(m, 4H); 3.34-3.81(m, 8H); 4.05-4.19 (2t, 4H); 6.20(m, 1H); 7.0-7.5(m, 6H) |
| 5 | D₂O: 0.93(t, 3H); 1.3-2.0(m, 6H); 2.6(m, 2H); 2.95(m, 4H); 3.17-3.62(m, 8H); 4.11(m, 4H); 7.1 (m, 3H); 7.4(m, 1H); 7.87(s, 1H); 7.97(s, 1H) |
| 6 | 1.13(t, 3H); 1.33(t, 3H); 1.93(m, 6H); 2.6 (t, 2H); 2.8(m, 4H); 3.35-3.82(m, 8H); 4.07-4.4 (m, 6H); 7.1-7.25(m, 3H); 7.5(m, 1H); 7.85(s, 2H) (m, 3H) |

Pharmacological Activity

The products which are the subject of the present invention are potent antihistaminics which are characterised in that they are free from sedative effects, in contrast to most known antihistaminics.

Antihistaminic Activity "In Vivo"

The antihistaminic activity was studied by determining the protection against the mortality caused by the product 48/80 in rats. This trial was performed according to the technique described by C. J. E. Niemegeers et al. (*Arch. Int. Pharmacodyn.*, 234, 164-176 (1978). The products which are the subject of the present invention are administered to the rats by the i.p. route. After 60 minutes, the compound 48/80 is administered (0.5 mg/kg, i.v.). The protective activity is defined as the survival of the rats 4 hours after the i.v. injection of the 48/80.

The activity of the products is studied at several doses in order to determine the dose which is capable of protecting 50% of the animals (ED-50).

Finally, the antihistaminic activity of the product of Example 1 is indicated. This activity is compared with that of difenhidramine, a reference antihistaminic.

| Antihistaminic activity "in vivo": Protection from 48/80-induced death | |
|---|---|
| Example no. | ED-50 (mg/kg, i.p.) |
| 1 | 0.04 |
| Difenhidramine | 5.4 |

Sedative Effect: 1) Irwin Test

To study the absence of sedative effect of the products which are the subject of the present invention, they were administered to rats by the i.p. route and the behaviour of the animals was observed according to the standards described in the S Irwin test (*Science.* 136, 123-128 (1962)).

The result obtained for the product of Example 1 is shown below in both evaluations reflecting the sedative effect:

Pas.: Passivity, sedation, prostration. Quantitative evaluation between 0 and 3. They are performed 1, 2 and 3 hours after the treatment.

Atax.: Ataxia, the modifications of coordination in movement are evaluated. The are evaluated between 0 and 3. They are performed 1, 2 and 3 hours after the treatment.

The results of the study of the sedative effect of the product of Example 1 of the present invention, are summarised below by way of example. This activity was compared with that of difenhidramine, a reference antihistaminic. This product exhibits a very weak sedative effect, unlike difenhidramine which proved toxic at a dose of 80 mg/kg, i.p., due to depressive effects on the CNS.

| Sedative effect: 1) Irwin Test | | | |
|---|---|---|---|
| | Dose | Effect | |
| Example no. | (mg/kg) | pas. | Atax. |
| 1 | (80) | 0 | 0.2 |
| Difenhidramine | (40) | 0 | 0.9 |
| | (80) | Toxic | |

Sedative Effect: 2) Potentiation of Pentobarbital-Induced Duration of Sleep

The study of the potentiation of the duration of sleep due to pentobarbital was performed according to the method described by L. E. Allen et al. (*Arz. Forsch.* 24, (6), (1974)). The studied products were administered orally. Sodium pentobarbital (35 mg/kg, s.c.) was administered one hour later and the length of time before the animals awoke was determined. The duration of sleep was compared with a control group of animals treated only with sodium pentobarbital.

To complete the studies which demonstrate the absence of sedative effect of the products which are the subject of the present invention, the activity of one of the products (Example 1) was compared, in this test, with the reference antihistaminic, difenhidramine. The results of this test with Example 1 and difenhidramine are presented below. It is evident that difenhidramine significantly potentiates the duration of sleep at a dose of 20 mg/kg, whereas Example 1 does not potentiate the pentobarbital-induced duration of sleep even at 160 mg/kg, the maximum dose tested.

| Sedative effect: 2) Potentiation of pentobarbital-induced duration of sleep | | | |
|---|---|---|---|
| Example no. | Dose (mg/kg, p.o) | Potentiation of duration of sleep | |
| 1 | 80 | 8% | N.S. |
| | 160 | 1% | N.S. |
| Difenhidramine | 10 | 22% | N.S. |
| | 20 | 38% | * |

N.S.: Not significant
*: Significant difference with the control group (p < 0.05)

A specific pharmaceutical dosage form of the derivatives which are the subject of the present invention, will be indicated below by way of example.

| Tablets Formula per tablet | |
|---|---|
| Compound of Example 1 | 10.00 mg |
| Lactose | 54.00 mg |
| Corn starch | 26.60 mg |

| Tablets Formula per tablet | |
|---|---|
| Microcrystalline cellulose | 18.00 mg |
| Polyvinylpyrrolidone | 6.00 mg |
| Croscarmellose sodium | 3.60 mg |
| Colloidal silicon dioxide | 0.60 mg |
| Magnesium stearate | 1.20 mg |
| | 120.00 mg |

We claim:

1. A compound derived from benzimidazole characterized in that it is of the formula I, and its therapeutically acceptable salts.

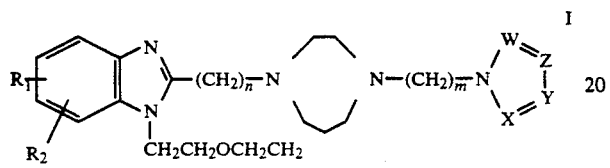

in which:

$R_1$ and $R_2$, which are identical or different, represent a hydrogen or a halogen atom, a lower alkyl radical, or a hydroxyl radical, n may take the values 0 or 1, m may take the values 2 to 4, X, Y, Z and W, which are identical or different, represent a nitrogen atom or a carbon atom linked to a hydrogen or to a halogen atom, or to another lower alkyl, hydroxyl, or sulphonic acid radical, or to a carboxyl or alkoxycarbonyl radical having up to two carbon atoms in its alkoxy position.

2. A compound which is chosen from the following group:

1-(2-ethoxyethyl)-2-{4-[4-(pyrazol-1-yl)butyl]homopiperazin-1-yl-methyl}benzimidazole, 1-(2-ethoxyethyl)-2-{4-[4-pyrrol-1-yl)butyl]homopiperazin-1-yl-methyl}benzimidazole, 1-(2-ethoxyethyl)-2-{4-[4-(4,5-dichloro-2-methylimidazole-1-yl)butyl]homopiperazin-1-yl-methyl}benzimidazole, 1-2(ethoxyethyl)-2-{4-[4-(pyrazol-1-yl)butyl]homopiperazin-1-yl}benzimidazole, 1-(2-ethoxyethyl)-2-{4-[4-(4-carboxypyrazole-1-yl)butyl]homopiperzin-1-yl}benzimidazole, 1-(2-ethoxyethyl)-2-{4-(4-ethyloxycarbonylpyrazole-1-yl)butyl]homopiperazin-1-yl}benzimidazole.

3. A pharmaceutical composition characterized in that it contains, in addition to a pharmaceutically acceptable carrier, at least one derivative of formula I or one of its physiologically acceptable salts, according to one of claim 1 or 2.

* * * * *